(12) United States Patent
Schmid et al.

(10) Patent No.: US 9,375,392 B2
(45) Date of Patent: Jun. 28, 2016

(54) USE OF THE GUANIDINIUM CATION AND LIGHT-EMITTING COMPONENT

(75) Inventors: Guenter Schmid, Hemhofen (DE); David Hartmann, Erlangen (DE); Andreas Kanitz, Hoechstadt (DE); Wiebke Sarfert, Herzogenaurach (DE)

(73) Assignee: OSRAM AG, München (DE)

( * ) Notice: Subject to any disclaimer, the term of this patent is extended or adjusted under 35 U.S.C. 154(b) by 990 days.

(21) Appl. No.: 13/575,270

(22) PCT Filed: Nov. 19, 2010

(86) PCT No.: PCT/EP2010/067829
§ 371 (c)(1),
(2), (4) Date: Oct. 22, 2012

(87) PCT Pub. No.: WO2011/088918
PCT Pub. Date: Jul. 28, 2011

(65) Prior Publication Data
US 2013/0035509 A1 Feb. 7, 2013

(30) Foreign Application Priority Data
Jan. 25, 2010 (DE) .......................... 10 2010 005 634

(51) Int. Cl.
*A61K 9/00* (2006.01)
*A61K 8/43* (2006.01)
*H01M 4/02* (2006.01)

(52) U.S. Cl.
CPC ... *A61K 8/43* (2013.01); *H01M 4/02* (2013.01)

(58) Field of Classification Search
None
See application file for complete search history.

(56) References Cited

U.S. PATENT DOCUMENTS

| | | | |
|---|---|---|---|
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 8,734,962 B2 * | 5/2014 | Adler ................. | C07F 15/0033 252/301.16 |
| 2002/0099157 A1 | 7/2002 | Stephan et al. | |
| 2003/0211389 A1 | 11/2003 | Schlaikjer | |
| 2006/0054886 A1 | 3/2006 | Bazan et al. | |
| 2007/0176148 A1 | 8/2007 | Park et al. | |

(Continued)

FOREIGN PATENT DOCUMENTS

| | | |
|---|---|---|
| DE | 10 2009 031 683 A1 | 3/2011 |
| DE | 102013202250 A1 | 8/2014 |
| EP | 1 363 345 A2 | 11/2003 |

(Continued)

OTHER PUBLICATIONS

Su, H-C., et al., "Decreased Turn-On Times of Single-Component Light-Emitting Electromechanical Cells by Tethering an Ionic Iridium Complex with Imidazolium Moieties," Chemistry—An Asian Journal, vol. 3, No. 11, Nov. 13, 2008, pp. 1922-1928.

(Continued)

*Primary Examiner* — Paul Dickinson
(74) *Attorney, Agent, or Firm* — Slater Matsil, LLP

(57) ABSTRACT

The invention relates to a use of the guanidinium cation and to a light-emitting component. This invention for the first time describes matrix materials and emitters for uses in organic electrochemical light-emitting cells containing a guanidinium cation unit. Guanidinium groups as a cationic system promise a wide electrochemical window and hence stable components. The route to guanidinium systems is described in detail in the literature.

7 Claims, 1 Drawing Sheet

(56) References Cited

U.S. PATENT DOCUMENTS

| | | |
|---|---|---|
| 2011/0187265 A1 | 8/2011 | De Cola et al. |
| 2012/0169213 A1 | 7/2012 | De Cola et al. |

FOREIGN PATENT DOCUMENTS

| | | |
|---|---|---|
| EP | 1 692 244 B1 | 4/2007 |
| EP | 1 904 508 B1 | 8/2009 |
| WO | WO 2005/019373 A2 | 3/2005 |
| WO | WO 2005/097942 A1 | 10/2005 |
| WO | WO 2005/097943 A1 | 10/2005 |
| WO | WO 2006/008976 A1 | 1/2006 |
| WO | WO 2006/013738 A1 | 2/2006 |
| WO | WO 2006/098120 A1 | 9/2006 |
| WO | WO 2007/004113 A2 | 1/2007 |
| WO | WO 2008/000726 A1 | 1/2008 |
| WO | WO 2008/141637 A2 | 11/2008 |
| WO | 2010007107 A1 | 1/2010 |

OTHER PUBLICATIONS

Coppo, P., et al., "White-Light Emission from an Assembly Comprising Luminescent Iridium and Europium Complexes," Angew. Chem. Int. Ed., vol. 44, 2005, pp. 1806-1810.

Handy, E., et al., "Solid-State Light-Emitting Devices Based on the Tris-Chelated Ruthenium(II) Complex. 2. Tris(bipyridyl)ruthenium(II) as a High-Brightness Emitter," Journal of the American Chemical Society, vol. 121, 1999, pp. 3525-3528.

Kwon, T-H., et al., "New Approach Toward Fast Response Light-Emitting Electrochemical Cells Based on Neutral Iridium Complexes via Cation Transport," Advanced Functional Materials, vol. 19, 2009, pp. 711-717.

Ouisse, T., et al., "Double-layer formation in organic light-emitting electrochemical cells," Journal of Applied Physics, vol. 92, No. 5, Sep. 1, 2002, pp. 2795-2802.

Pei, Q., et al., "Polymer Light-Emitting Electrochemical Cells," Science, New Series, vol. 269, No. 5227, Aug. 25, 1995, pp. 1086-1088.

\* cited by examiner

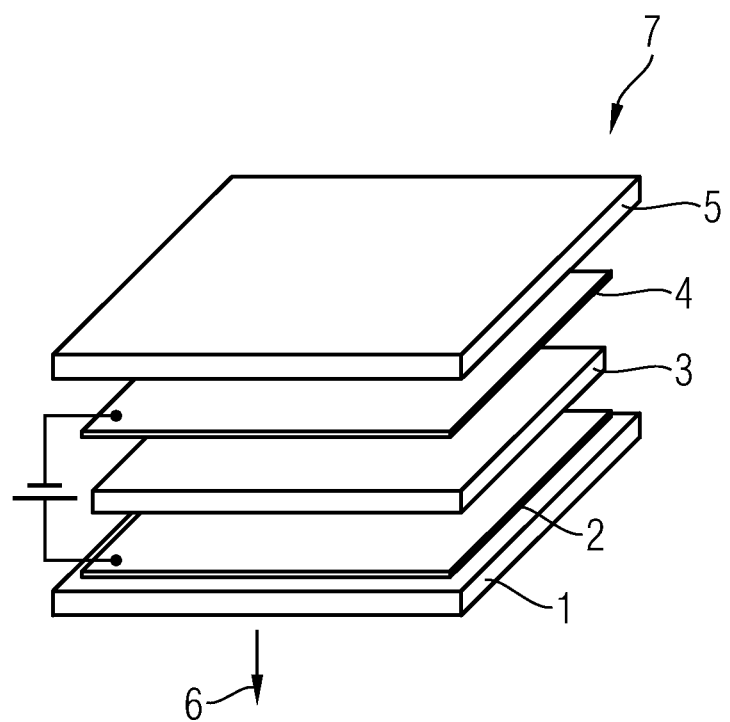

USE OF THE GUANIDINIUM CATION AND LIGHT-EMITTING COMPONENT

This patent application is a national phase filing under section 371 of PCT/EP2010/067829, filed Nov. 19, 2010, which claims the priority of German patent application 10 2010 005 634.0, filed Jan. 25, 2010, each of which is incorporated herein by reference in its entirety.

TECHNICAL FIELD

The invention relates to a use of the guanidinium cation and to a light-emitting component.

BACKGROUND

Organic-based light-emitting components are known, but there is a need to optimize these with regard to stability and lifetime on the one hand, and with regard to costs on the other hand.

Aside from the significance of the guanidinium cation as a dehydrant of proteins and in biochemistry, there are applications of the guanidinium cation in batteries and electrochemical cells. This use of guanidinium salts is described, for example, in European Patent Publication No. EP 1363345 A2 and U.S. Patent Publication No. 2003/0211389 A1. The guanidinium salts serve here for production of electrolytes for the electrochemical storage of charge in accumulators and batteries.

In this application, a key factor is the intrinsic conductivity of the conductive salt, which should be at a maximum in order to be able to effectively store the charge.

However, there are very many guanidinium salts with low intrinsic conductivity, for which there is currently no known use other than as a synthesis unit and for dehydration in proteins.

SUMMARY OF THE INVENTION

It is therefore an object of the present invention to find an application of the guanidinium cation in which guanidinium salts with low conductivity also exhibit high efficiency.

The solution to the problem and the subject matter of the invention is the use of the guanidinium salts in a light-emitting organic electronic component. The invention also provides an organic electrochemical cell which comprises, in the active organic layer thereof, a compound containing a guanidinium cation.

BRIEF DESCRIPTION OF THE DRAWING

The lone FIGURE shows the structure of an OLEEC in schematic form.

DETAILED DESCRIPTION OF ILLUSTRATIVE EMBODIMENTS

The central nitrogen atom of the guanidinium base structure always bears a positive charge which, according to the structure, may be delocalized over the entire compound, or is localized on the central carbon surrounded by the three guanidinium nitrogen atoms. In the latter case, the charge is delocalized only over 4 atoms (1×N and 3×C).

Emitters and matrix materials according to this invention contain, as the central unit, at least one guanidinium unit with positive charge as shown below. The positive charge is naturally delocalized at least within the guanidinium unit.

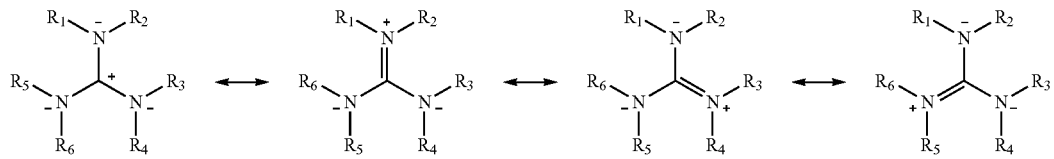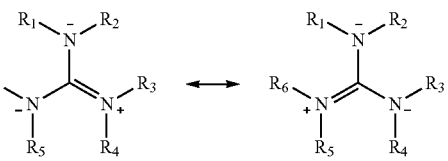

This is the central guanidinium unit of the inventive matrix and emitter materials, where all radicals are R=independently H, saturated or unsaturated, branched alkyl radicals, unbranched alkyl radicals, fused alkyl radicals, cyclic alkyl radicals, completely or partially substituted unbranched, branched, fused and/or cyclic alkyl radicals, alkoxy groups, amines, amides, esters, carbonates, aromatics, completely or partially substituted aromatics, heteroaromatic compounds, fused aromatics, completely or partially substituted fused aromatics, heterocycles, completely or partially substituted heterocycles, fused heterocycles, halogens, pseudohalogens.

All substituents $R_1$, $R_2$, R+ may independently be selected from the abovementioned radicals, and are preferably $C_1$ to $C_{20}$, fused, e.g., decahydronaphthyl, adamantyl, cyclic, cyclohexyl, or completely or partially substituted alkyl radical, preferably $C_1$ to $C_{20}$. These chains or groups may bear various end groups, for example, charged end groups such as $SO_x^-$, $NR^+$ and so forth.

The alkyl radicals may in turn bear groups such as ether, ethoxy, methoxy, etc., ester, amide, carbonate, etc., or halogens, preferably fluorine. $R_1$, $R_2$ and $R_3$ shall not, however, be restricted to alkyl radicals, and may instead equally include substituted or unsubstituted aromatic systems, for example phenyl, biphenyl, naphthyl, phenanthryl, benzyl and so forth.

The substituents $R_1$ to $R_6$ may each independently be of aliphatic, aromatic or complex structure.

By varying the $R_1$ to $R_6$ radicals, it is possible to obtain various types of ligand systems suitable for the emitter systems in the inventive component. $R_1$ to $R_6$ may each independently be H (to a restricted degree, since guanidinium salts are normally fully substituted methyl, ethyl, generally unbranched, branched, fused (decahydronaphthyl), cyclic (cyclohexyl) or completely or partially substituted alkyl radicals ($C_1$-$C_{20}$). These alkyl radicals may contain ether groups (ethoxy, methoxy, etc.), ester, amide, carbonate groups etc., or else halogens, especially F. The scope of the invention also includes substituted or unsubstituted aliphatic rings or ring systems, such as cyclohexyl.

$R_1$ to $R_6$ are not restricted to saturated systems, but also include substituted or unsubstituted aromatics such as phenyl, diphenyl, naphthyl, phenanthryl etc., and benzyl etc., respectively. A compilation of heterocycles which are possible substituents is shown in table 1. For the sake of simplicity, only the base structure of the aromatics is shown. In principle, this base structure may be substituted by further R radicals, which can be derived analogously from the $R_1$ to $R_6$ radicals defined here.

TABLE 1
| | |
|---|---|
|  Furan | 5 |
|  Thiophene | 10 |
|  Pyrrole | 15 |
|  Oxazole | 20 |
|  Thiazole | 25 |
|  Imidazole | 30 |
|  Isoxazole | 35 |
|  Isothiazole | 40 |
|  Pyrazole | 45 |
| 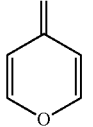 Pyridine | 50 |
|  Pyrazine | 55 |
TABLE 1-continued
| | |
|---|---|
| 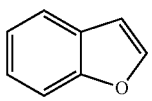 Pyrimidine | |
|  1,3,6 Triazine | |
| 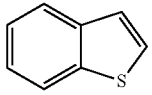 Pyrylium | |
|  alpha-Pyrone | |
| 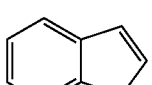 gamma-Pyrone | |
|  Benzo[b]furan | |
| 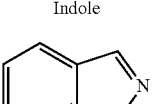 Benzo[b]thiophene | |
|  Indole | |
| 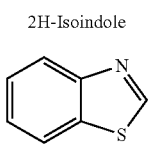 2H-Isoindole | |
|  Benzothiazole | |

TABLE 1-continued
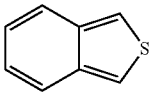
2-benzothiophene
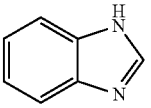
1H-benzimidazole
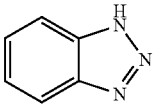
1H-benzotriazole
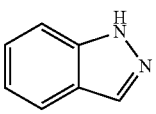
1H-indazole
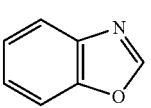
1,3-benzoxazole
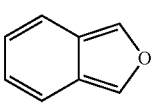
2-benzofuran
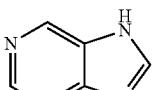
7H-purine
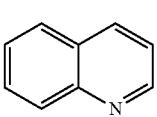
Quinoline
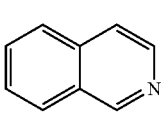
Iso-quinoline
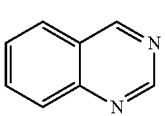
Quinazoline
TABLE 1-continued
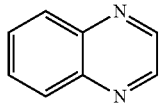
Quinoxaline
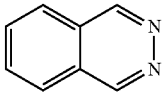
phthalazine
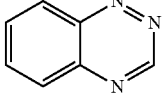
1,2,4-benzotriazine
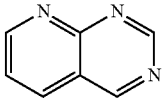
Pyrido[2,3-d]pyrimidine
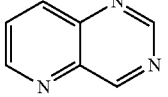
Pyrido[3,2-d]pyrimidine
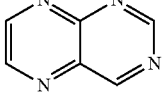
pteridine
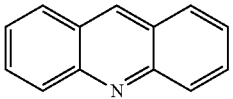 [SMILES: c1ccc2nc3ccccc3cc2c1]
acridine
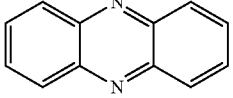
phenazine
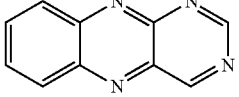
benzo[g]pteridine
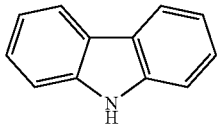 [SMILES: c1ccc2c(c1)[nH]c1ccccc12]
9H-carbazole TABLE 1-continued

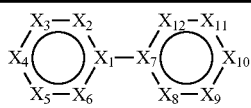

Bipyridine & derivatives (0-2$X_i$/Ring = N)

Table 1 shows a selection of substituted and unsubstituted heterocycles which are independently possible as $R_1$, $R_2$ radicals. For the sake of simplicity, only the base unit is shown. The bond to the ligand may be at any site capable of bonding on the base structure.

R+ introduces the positive charge on the nitrogen atom and is preferably a substituted or unsubstituted aliphatic radical, for example a methyl, ethyl, or a general straight-chain or branched, fused (decahydronaphthyl, adamantyl), cyclic (cyclohexyl) alkyl radical which may be completely or partially substituted and comprises alkyl units having, for example, 1 to 20 carbon atoms.

Preferably, but without restriction, the anions required for compensation of the positive charge are selected from: fluoride, chloride, bromide, iodide, sulfate, phosphate, carbonate, trifluoromethanesulfonate, trifluoroacetate, tosylate, bis(trifluoromethylsulfone)imide, tetraphenylborate, $B_9C_2H_{11}^{2-}$; hexafluorophosphate, tetrafluoroborate, hexafluoroantimonate, tetrapyrazolatoborate.

The guanidinium derivatives may themselves comprise or consist of fused ring systems. A fully annulated system is shown below.

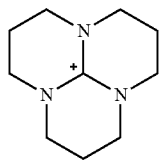 [SMILES: C1CN2CCCN3CCCN(C1)[C+]23]

A fully annulated system with a guanidinium central unit is shown here. For the sake of simplicity, all possible substituents have been omitted. In principle, any C—H bond can be replaced by a C—R bond.

A whole series of systems can be derived from the structures shown, all of which contain the guanidinium base structure. Shown below by way of example are fused systems which have been derived from imidazole.

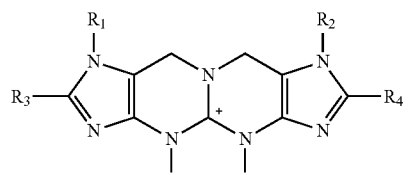

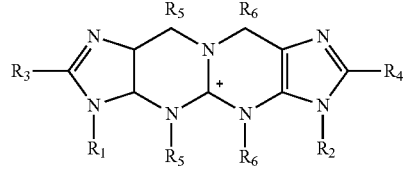

For the sake of clarity, the substituents on the imidazole groups are neglected.

Shown above are annulated guanidinium cations with fused-on imidazole rings or partly hydrogenated imidazoles.

The structures below show a selection from the variety of derivable structures in the context of the invention.

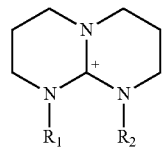

FIG. 6a

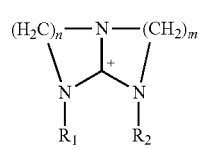

FIG. 6b

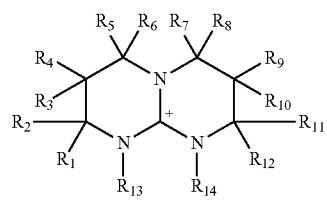

FIG. 6c

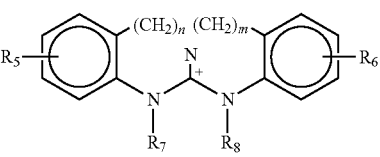

FIG. 7a

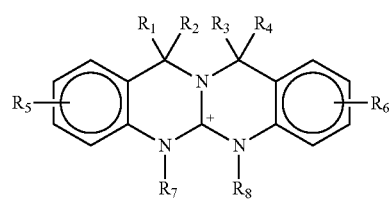

FIG. 7b

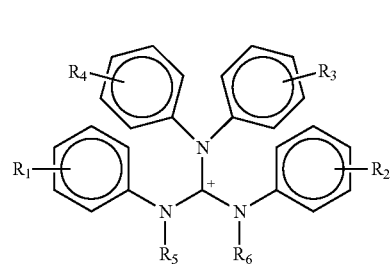

FIG. 8a

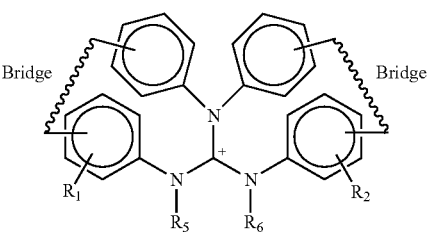

FIG. 8b

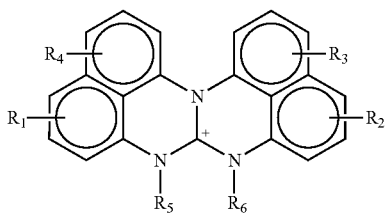

FIG. 9c

The compounds discussed to date serve principally as matrix materials since they do not contain any emissive units.

At the same time, it is entirely conceivable in the context of the invention that the aromatic substituents (which are conjugated or nonconjugated to the guanidinium core) may have an appropriate size or may form a donor-acceptor pair which may constitute a fluorescent unit which can also be electrically excited analogously to the OLED.

The active organic layer of an OLEEC comprises a matrix and an emitter material bonded (physically or chemically) therein. According to the invention, a guanidinium cation may be present either in the matrix material or in the emitter material, or else in both.

The typical structure of an organic electrochemical cell OLEEC comprises a transparent substrate, a transparent electrode thereon, which is usually used as the anode, the active organic layer thereon, which has, for example, a layer thickness in the range from 100 nm to 1 μm. On the active organic layer lies the second electrode, which is not necessarily transparent and is usually connected as the cathode.

In contrast to the widely known OLEDs which have already been discussed many times, the latter comprising electron/hole-transporting layers and electron/hole-blocking layers in addition to the emitting layers, a particular feature of the OLEECs is a much simpler construction, since usually only one organic active layer is required here.

In the organic light-emitting diodes (OLEDs), more particularly in the case of the OLEDs formed with what are called small molecules, what is called a multilayer structure is achieved because, in addition to the light-emitting layer, efficiency-enhancing layers such as hole and/or electron injection layers or blocker layers are arranged between the electrodes for better transfer of the charge carriers. Often, high-reactivity materials are used because the materials feature a low work function. Therefore, hermetic encapsulation is essential in the case of OLEDs.

Since the reactive electrodes of the OLED can be dispensed with in the OLEECs, the overall encapsulation problem is not as difficult in the case of the OLEECs as in the case of the OLEDs. The OLEECs are therefore considered to be a promising substitute for the OLEDs.

In OLEDs, uncharged organic, inorganic and/or organometallic compounds are utilized as matrix, emitter and dopants. In contrast, the material basis of organic light-emitting electrochemical cells is ionic in nature. For formation of the component, the ionic emitter systems are introduced either into an uncharged (for example, uncharged polymers such as polymethylmethacrylate) or ionic (for example, ionic liquids) matrix and connected to contacts by means of two electrodes.

In quite general terms, organic electroluminescent elements have at least one organic layer present between two electrodes. As soon as voltage is applied to the electrodes, electrons are injected from the cathode into the lowermost unoccupied molecular orbital of the organic light-emitting layer and migrate to the anode.

Correspondingly, holes are injected from the anode into the highest occupied molecular orbital of the organic layer and migrate accordingly to the cathode. In the cases where migrating hole and migrating electron meet a light-emitting substance within the organic light-emitting layer, an exciton forms, which decomposes with emission of light. In order that the light can leave the electroluminescent element at all, at least one electrode has to be transparent; in most cases, one electrode is composed of indium tin oxide, which is used as the anode. The ITO layer is normally deposited on a glass carrier.

The degradation mechanisms in OLEECs and the development of stable matrix and emitter systems for OLEECs is currently the subject of numerous studies. Emitter and matrix systems with guanidinium units can be expected to give an increase in the lifetime of OLEECs due to the stability thereof.

In the case of use of the salts formed from a guanidinium cation for electrochemical cells, the intrinsic conductivity should be relatively low since an excessive leakage current would otherwise flow through the component. The guanidinium compounds presented in this invention disclosure have usually low intrinsic conductivities, but enable charge transport through the component by "hopping." More particularly, they enable charge transport via the matrix to the emitter.

In an advantageous embodiment of the invention, the emitter also comprises, independently of the matrix, a guanidinium unit.

The OLEECs, as already mentioned, in principle need only one active organic layer, which can additionally be applied via methods suitable for mass production, such as simple coating methods, for example spin-coating, knife-coating, dipping, slot die coating, or printing methods such as screen printing, flexographic printing, intaglio printing, inkjet printing.

The typical layer thickness is 10 to 200 nm, but may also assume other values, for example up to 1,000 nm. Since the electrical field in OLEECs declines principally over the electrodes and not over the light-emitting layer, layer thicknesses above 1,000 nm can also still give good components. Preferably, for OLEECs, there is no need to use the reactive electrodes such as barium, calcium, lithium fluoride, cesium fluoride, magnesium etc.; instead, it is possible to use air-stable metals such as gold, palladium, platinum, aluminum, magnesium, silver, copper, nickel, iron, ITO, AZO and alloys thereof.

In the OLEECs, the active layer is a mixture of a conductor for ions and electrons and an emitting species. Ionic transition metal complexes (iTMCs) combine these requirements and are therefore often used in OLEEC applications. A typical representative is ruthenium trisbipyridine hexafluorophosphate $[Ru(bpy)_3]^{2+}(PF_6^-)_2$ described by Q. Pei, G. Yu, C. Zhang, Y. Yang, A. J. Heeger in Science, Vol. 269, 1086-1088, 1995.

When an electrical field is applied to iTMCs, the ions regroup in the electrical field. As a result, a high electrical field is formed at the electrodes, such that both contacts become ohmic contacts, which facilitates charge transfer into the organic layer. The charges are then transported through the iTMC layer by "hopping." When holes and electrons meet, they recombine to form excitons, which results in light emission.

Most iTMC materials which are known to date have ruthenium, osmium, copper or iridium central atoms.

The conventional OLED complexes are abbreviated hereinafter by the formula I shown. Representing all emitting systems, iridium complexes with the coordination number of 6 are depicted. Taking account of the coordination number, for example platinum 4, europium usually 8, Os 6, the considerations also apply to other systems. The carbon σ-bond is shown as a solid line, and the coordinate bond of the bidentate ligand as a broken line. The formula shows these conditions in highly schematic form. "A" denotes a substituted or unsubstituted aromatic or heteroaromatic compound capable of the bonding conditions mentioned. All aromatics may be varied independently of one another as shown in the prior art. The solid bond to carbon or nitrogen is formed from a C—H or N—H precursor by hydrogen elimination (cyclometalation). The broken line indicates either a carbene carbon or a nitrogen or phosphorus which coordinates through a free electron pair.

Formula I

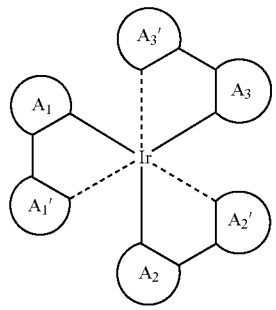

According to the invention, the emitter units shown below are, for example, bonded via a guanidinium unit and/or have a guanidinium radical as the $R_x$ radical. Thus, as is also possible through R+ on the nitrogen, the generally uncharged emitters receive a charge.

The conventional iridium emitters exhibit at least one phenylpyridine ligand: the phenylpyridine ligand is bonded to the central atom in the manner of a cyclometalation to form a direct metal-carbon bond. Some typical representatives are shown below:

Examples of cyclometalated iridium-based emitters are:

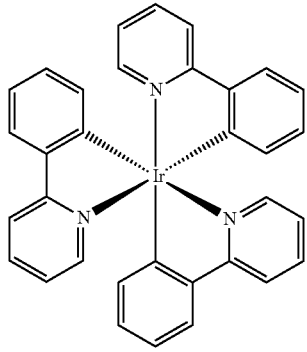

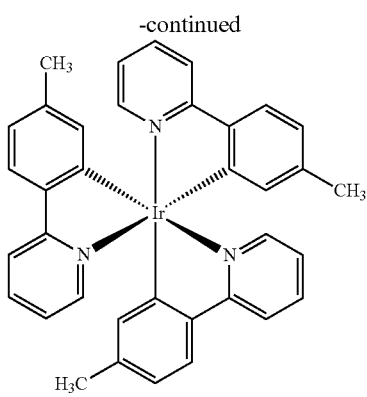

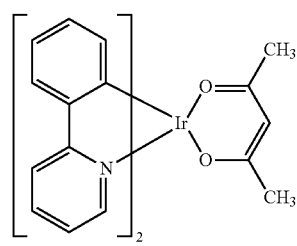

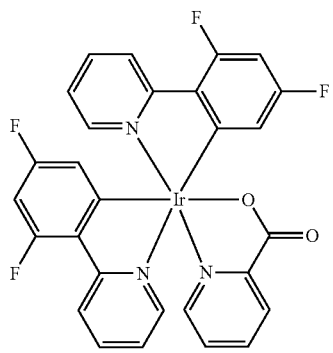

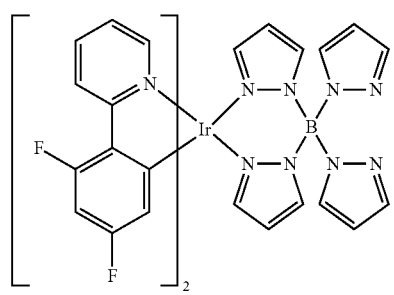

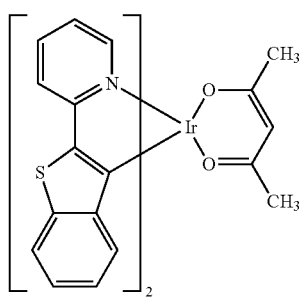

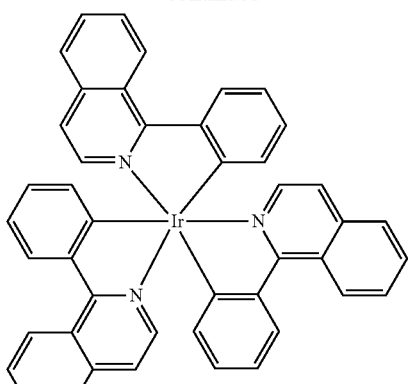
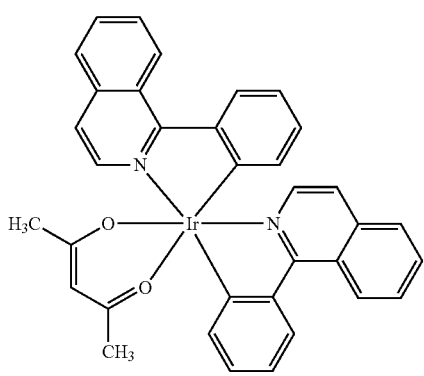
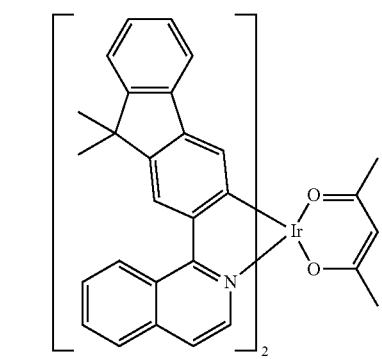
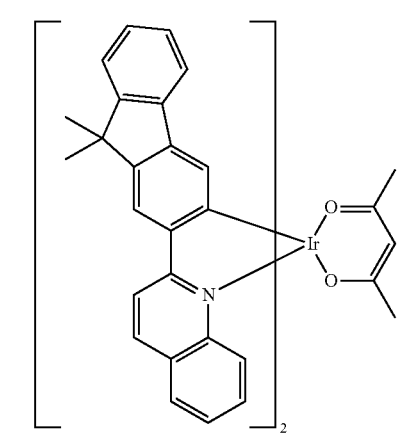
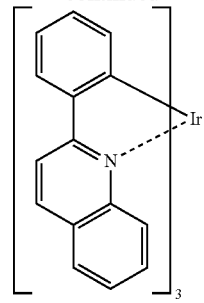
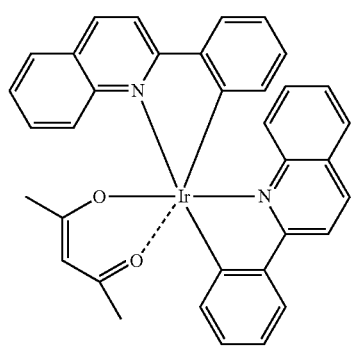
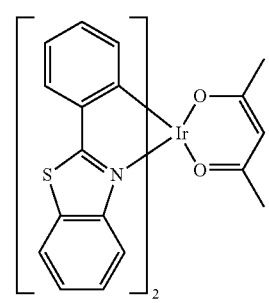
These are typical examples of cyclometalated iridium-based emitters. A further representative is the iridium-carbene complex:
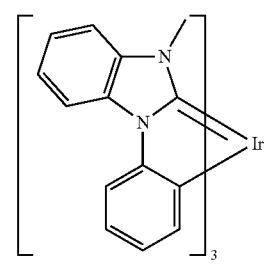
Emitting systems are not restricted to iridium. There are also examples of uncharged emitters with lanthanides, especially europium and other heavy metals, for example osmium.

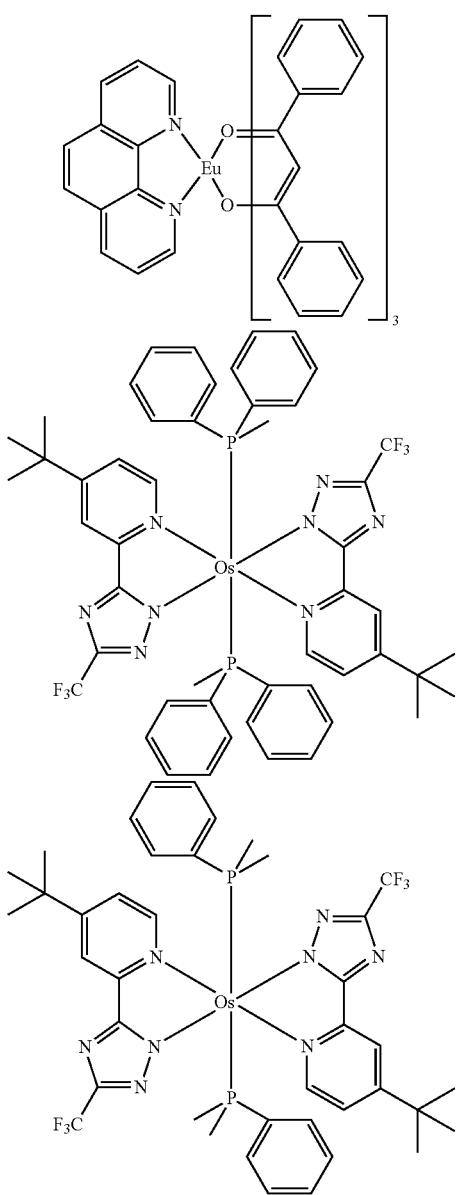

The base structures shown can be bonded via guanidinium units, so as to form ionic emitters which are iridium-based or non-iridium-based.

In the formulae shown above, the phenylpyridine ligand is preferably bonded to the central atom in the manner of a cyclometalation, forming a direct metal-carbon bond. Some typical iridium complexes with cyclometalation are shown here. Fluorination of the phenylpyridine ligand shifts the emission in the spectrum in the blue direction. Known examples of the fluorinated species are bis(2,4-difluorophenyl-2-pyridyl)iridium(III) picolinate (FIrPic) or bis(2,4-difluorophenylpyridinato)tetrakis(1pyrazolyl)borate iridium (III) (FIr6).

For OLED applications, there are very many emitters; examples mentioned here include typical cyclometalating ligands as described, for example, in International Patent Publication Nos. WO 2005/097942 A1, WO 2006/013738 A1, WO 2006/09812 A1, WO 2006/008976A1, WO 2005/ 097943 A1 (Konica Minolta) or U.S. Pat. No. 6,902,830, U.S. Pat. No. 7,001,536, U.S. Pat. No. 6,830,828 (UDC). They are all bonded to iridium or another central atom via an N^C unit. Example: 2-Phenylpyridine or 2-phenylimidazole and related structures, for example benzimidazole or phenanthridine. Particularly the 2-phenylimidazole derivatives are known for a shift in the emission to the blue-green to blue spectral region.

The known ligands L may have, for example, a further carbene functionality which serves as a source of deep blue emission. Examples of these ligands L can be found in publications International Patent Publication No. WO 2005/ 19373, European Patent Publication No. EP 1692244 B1 and International Patent Publication No. WO 2008/000726 A1.

Further examples of possible ligands L are known from publications European Patent Publication No. EP 1904508 A2, International Patent Publication Nos. WO 2007/004113 A2, WO 2007/004113 A3, and these ligands L are also shown in the context of charged metal complexes having at least one phenylpyridine ligand with appropriate donor groups such as dimethylamino. These compounds exhibit an elevated LUMO level of the complex, with introduction of acceptor groups, for example 2,4-difluoro, into the phenyl ring in order to lower the level of the HOMO orbital. It is shown that, through the variation of the ligands and substituents thereof, the emission color can be varied through the entire visible spectrum.

The as yet unpublished German Patent Publication No. DE 10 2009 031 683.3 discloses iridium-carbene complexes. In addition, emitting systems are of course not restricted to iridium; instead, it is also possible to form uncharged emitters with lanthanides, especially europium, and other heavy metals such as osmium.

Examples of known uncharged emitters:

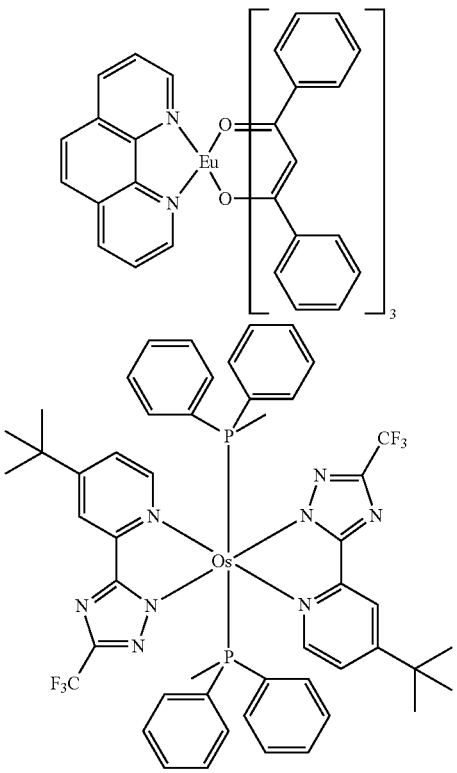

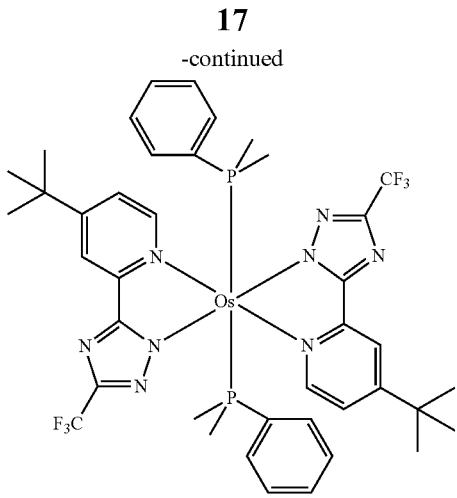

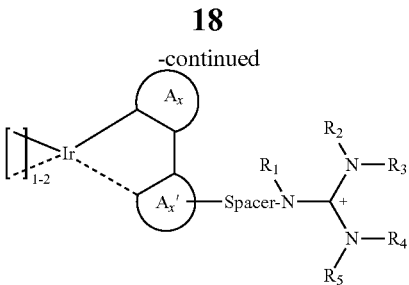

General formula II of the emitter materials, where x=1-3.]]
General formula II of the emitter materials, where x=1-3.

Correspondingly, metals other than Ir can be used, for example but without restriction Eu, Nd, Gd, Re, Os, Pt, Au, Hg, and Ru, Pd, Ag.

The two further ligands may each independently be analogous to the known imidazolinium-substituent ligands, or are selected from the conventional cyclometalating ligands as described, for example, in International Patent Publication Nos. WO 2005/097942 A1, WO 2006/013738 A1, WO 2006/098120 A1, WO 2006/008976 A1, WO 2005/097943 A1, (Konica Minolta) or U.S. Pat. No. 6,902,830, U.S. Pat. No. 7,001,536, U.S. Pat. No. 6,830,828 (UDC). They are all bonded to iridium via an N^C unit (example: 2-phenylpyridine or 2-phenylimidazole and related structures, for example benzimidazole or phenanthridine).

The spacers used may be:

a) aliphatic chains such as —$(CH_2)_n$— where n=1-20, preferably n=1-5, b) fluorinated alkyl chains having 1-12 carbon atoms in the chain, more preferably 6-10, c) unsaturated alkyl chains having 1-20 carbon atoms and conjugated or nonconjugated double bonds, d) unsaturated alkyl chains having 1-20 carbon atoms and conjugated or nonconjugated triple bonds, also in conjunction with aromatics, e) instead of an alkyl chain, it is also possible to use a polyethylene glycol, polyethylenediamine, polyester, polyurethane, or polyvinylidenephenylene chain, f) chains which contain aromatics, thus more particularly making it possible also to adjust the geometry of the imidazolinium group compared to the emitter, g) mixed variants of a-f, h) further spacers which are obvious to the person skilled in the art but are not specifically mentioned here.

The sole FIGURE shows the structure of an OLEEC in schematic form.

An OLEEC 7 is in principle of simpler construction than the OLED and is in most cases realizable by a simple introduction of an organic layer 3 between two electrodes 2 and 4 and subsequent encapsulation 5. On application of voltage, light 6 is emitted. The preferably one active emitting layer 3 of an OLEEC consists of a matrix into which an emitting species has been embedded. The matrix may consist of an insulator or of a material which is either an ion conductor with electrolyte properties or an inert matrix (insulator). The emitting species is/are one or more ionic transition metal complexes (iTMCs for short), for example, the compounds with a guanidinium cation, and/or has been embedded in a matrix material which, according to the present invention, may also again contain a guanidinium cation.

On the transparent substrate 1 is the lower electrode layer 2, for example, the anode. Above this is the actually active emitting layer 3, and above that the second electrode 4. For better performance and processing, the emitter material (iTMC) which forms the active layer 3, i.e., the phosphores- Generally, all radicals are: R=independently H, branched alkyl radicals, unbranched alkyl radicals, fused alkyl radicals, cyclic alkyl radicals, completely or partially substituted unbranched, branched, fused and/or cyclic alkyl radicals, alkoxy groups, amines, amides, esters, carbonates, aromatics, completely or partially substituted aromatics, hetero aromatic compounds, fused aromatics, completely or partially substituted fused aromatics, heterocycles, completely or partially substituted heterocycles, fused heterocycles, halogens, pseudohalogens.

All substituents $R_1$, $R_2$, R+ may each independently be selected from the abovementioned radicals, preferably $C_1$ to $C_{20}$, fused, e.g., decahydronaphtyl, adamantyl, cyclic, cyclohexyl, or fully or partially substituted alkyl radical, preferably $C_1$ to $C_{20}$. These chains or groups may bear various end groups, for example charged end groups such as $SO_x^-$, $NR^+$ and so forth.

The alkyl radicals may in turn bear groups such as ether, ethoxy, methoxy, etc., ester, amide, carbonate, etc., or halogens, preferably fluorine. $R_1$, $R_2$ and $R_3$ however, shall not be restricted to alkyl radicals, but may instead equally comprise substituted or unsubstituted aromatic systems, for example phenyl, biphenyl, naphthyl, phenanthryl, benzyl, and so forth.

There follows a description of guanidinium cations which are part of a phosphorescent emitter system.

For this purpose, according to the general formula I shown above, at least one of the aromatic systems A is coupled to a guanidinium unit by means of a spacer. Thus, at least one of the conventional substituents in the ligands is replaced by a guanidinium unit.

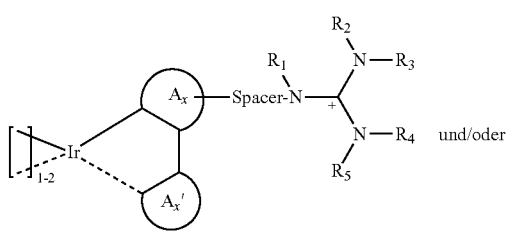

cent metal complex, is dissolved in a solvent together with a matrix material. Preferably, but without restriction, the following solvents are used: acetonitrile, tetrahydrofuran (THF), toluene, ethylene glycol diethyl ether, butoxyethanol, chlorobenzene, propylene glycol methyl ether acetate, further organic and inorganic and polar or nonpolar solvent mixtures are also usable in the context of the invention. The soluble matrix materials which are used in conjunction with iTMCs are, for example, polymers, oligomers and ionic liquids.

The matrix materials used for the construction of an OLEEC according to the invention are preferably ionic liquids which likewise contain a guanidinium unit. The inventive emitters therefore dissolve very readily in the matrix.

The matrix materials used for the construction of an OLEEC are ionic liquids, which likewise preferably but without limitation contain a guanidinium unit. Alternatively and additionally, it is possible to use matrix materials which contain, for example, imidazolinium cations. The inventive emitters therefore have very good solubility in the matrix.

Preferably, but without restriction, it is possible to use the "simple" anions selected from: fluoride, chloride, bromide, iodide, sulfate, phosphate, carbonate, trifluoromethanesulfonate, trifluoroacetate, tosylate, bis(trifluoromethylsulfone)imide, tetraphenylborate, $B_9C_2H_{11}{}^2$; hexafluorophosphate, tetrafluoroborate, hexafluoroantimonate, tetrapyrazolatoborate. The scope of the invention also includes complex anions, for example $Fe(CN)_6{}^{3-}$, $Fe(CN)_6{}^{4-}$, $Cr(C_2O_4)^{3-}$, $Cu(CN)_4{}^{3-}$, $Ni(CN)_4{}^{2-}$.

It is also possible to couple the guanidinium unit to sulfonate, pyridinium, imidazolinium.

Tae-Hyuk Kwon, Yong Ho Oh, Ik-Soo Shin, and Jon-In Hong, Adv. Mater. 19, 1-7, 2009.

P. Coppo, M. Duati, V. N. Kozhevnikov, J. W. Hofstraat, L. De Cola, Angew. Chemie Int. Engl. 44, 1806, 2005.

The table below lists some typical representatives of ionic liquids:

1-benzyl-3-methylimidazolium hexafluorophosphate
1-butyl-2,3-dimethylimidazolium hexafluorophosphate
1-butyl-3-methylimidazolium hexafluorophosphate
1-ethyl-3-methylimidazoliuin hexafluorophosphate
1-hexyl-3-methylimidazolium hexafluorophosphate
1-butyl-1-(3,3,4,4,5,5,6,6,7,7,8,8,8-tridecafluorooctyl)imidazolium hexafluorophosphate
1-methyl-3-(3,3,4,4,5,5,6,6,7,7,8,8,8-tridecafluorooctyl)imidazolium hexafluorophosphate
1-methyl-3-octylimidazolium hexafluorophosphate
1-butyl-2,3-dimethylimidazolium tetrafluoroborate
1-butyl-3-methylimidazolium tetrafluoroborate
1-ethyl-3-methylimidazolium tetrafluoroborate
1-hexyl-3-methylimidazolium tetrafluoroborate
1-methyl-3-octylimidazolium tetrafluoroborate
1-butyl-3-methylimidazolium trifluoromethanesulfonate
1-ethyl-3-methylimidazolium trifluoromethanesulfonate
1,2,3-trimethylimidazolium trifluoromethanesulfonate
1-ethyl-3-methyl-imidazolium bis(pentafluoroethylsulfonyl)imide
1-butyl-3-methylimidazolium bis(trifluoromethylsulfonyl)imide
1-butyl-3-methylimidazolium methanesulfonate
tetrabutylammonium bis-trifluoromethanesulfonimidate
tetrabutylammonium methanesulfonate
tetrabutylammonium nonafluorobutanesulfonate
tetrabutylammonium heptadecafluorooctanesulfonate
tetrahexylammonium tetrafluoroborate
tetrabutylammonium trifluoromethanesulfonate
tetrabutylammonium benzoate
tetrabutylammonium chloride
tetrabutylammonium bromide
1-benzyl-3-methylimidazolium tetrafluoroborate
trihexyltetradecylphosphonium hexafluorophosphate
tetrabutylphosphonium methanesulfonate
tetrabutylphosphonium tetrafluoroborate
tetrabutylphosphonium bromide -continued 1-butyl-3-methylpyridinium bis(trifluoromethylsulfonyl)imide
1-butyl-4-methylpyridinium hexafluorophosphate
1-butyl-4-methylpyridinium tetrafluoroborate sodium tetraphenylborate
tetrabutylammonium tetraphenylborate
sodium tetrakis(1-imidazolyl)borate
cesium tetraphenylborate This invention for the first time describes matrix materials and emitters for uses in organic electrochemical light-emitting cells containing a guanidinium cation unit. Guanidinium groups as a cationic system promise a broad electrochemical window and hence stable components. The route to guanidinium systems is described in detail in the literature.

The invention claimed is:

1. An organic electrochemical cell comprising:
a first electrode layer;
a second electrode layer; and
an active organic layer between the first electrode layer and the second electrode layer,
wherein a compound containing a guanidinium cation is present in the active organic layer,
wherein a salt containing the guanidinium cation exhibits the following structural unit:

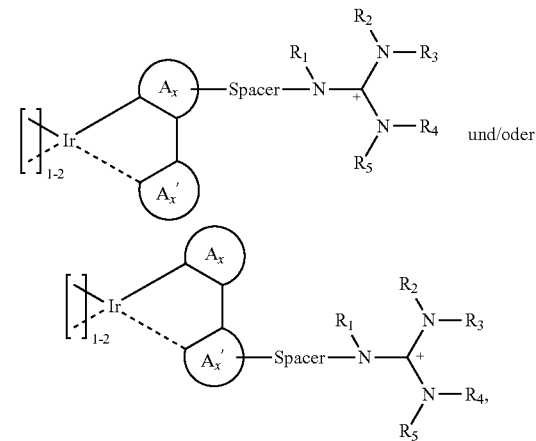

wherein $A_x$ and $A_{x'}$ are chosen from a substituted or unsubstituted aromatic or heteroaromatic compound,
where Ir is a metal,
wherein

are ligands coordinated to Ir,
wherein each spacer comprises a spacer selected from the group consisting of:
a) aliphatic chains,
b) fluorinated alkyl chains having 1-12 carbon atoms in the chain,
c) unsaturated alkyl chains having 1-20 carbon atoms and conjugated or nonconjugated double bonds,
d) unsaturated alkyl chains having 1-20 carbon atoms and conjugated or nonconjugated triple bonds, also in conjunction with aromatics,
e) a polyethylene glycol, polyethylenediamine, polyester, polyurethane, or polyvinylidenephenylene chain, f) chains which contain aromatics,
g) mixed variants of a-f, and
wherein $R_1$ to $R_5$ comprises a substituent of aliphatic or aromatic structure.

2. The organic electrochemical cell according to claim 1, wherein the salt containing the guanidinium cation is present in an emitter material of the active organic layer.

3. The organic electrochemical cell according to claim 1, wherein the salt containing the guanidinium cation is present in a matrix material of the active organic layer.

4. The organic electrochemical cell according to claim 1, wherein the salt containing the guanidinium cation exhibits the following structural unit:

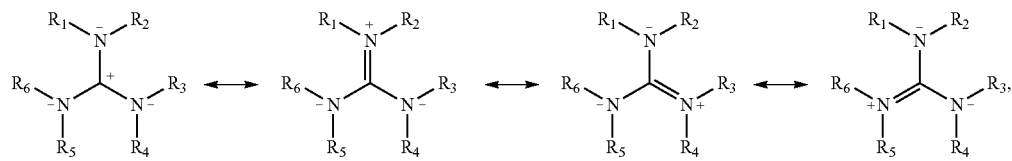

where substituents $R_1$ to $R_6$ are each independently of an aliphatic structure or an aromatic structure.

5. The organic electrochemical cell according to claim 4, wherein the substituents $R_1$ to $R_6$ are each independently:
R=independently H, saturated or unsaturated, branched alkyl radicals, unbranched alkyl radicals, fused alkyl radicals, cyclic alkyl radicals, completely or partially substituted unbranched, branched, fused and/or cyclic alkyl radicals, alkoxy groups, amines, amides, esters, carbonates, aromatics, completely or partially substituted aromatics, heteroaromatic compounds, fused aromatics, completely or partially substituted fused aromatics, heterocycles, completely or partially substituted heterocycles, fused heterocycles, halogens, pseudohalogens.

6. The organic electrochemical cell according to claim 1, wherein
the spacer comprises an aliphatic chain of $-(CH_2)_n-$ where n=1-20.

7. The organic electrochemical cell according to claim 1, wherein the substituent R comprises H, saturated or unsaturated, branched alkyl radicals, unbranched alkyl radicals, fused alkyl radicals, cyclic alkyl radicals, completely or partially substituted unbranched, branched, fused and/or cyclic alkyl radicals, alkoxy groups, amines, amides, esters, carbonates, aromatics, completely or partially substituted aromatics, heteroaromatic compounds, fused aromatics, completely or partially substituted fused aromatics, heterocycles, completely or partially substituted heterocycles, fused heterocycles, halogens, pseudohalogens.

* * * * *